(12) United States Patent
Bouvyn

(10) Patent No.: US 6,201,602 B1
(45) Date of Patent: Mar. 13, 2001

(54) DETECTION OF FOREIGN FIBRES AND FOREIGN MATERIALS BASED ON AN ABSORPTION MEASUREMENT OF LIGHT AND CORRESPONDING DETECTION METHOD

(75) Inventor: Patrick Bouvyn, Waregem (BE)

(73) Assignee: Barco B.V., Poperinge (BE)

( * ) Notice: Subject to any disclaimer, the term of this patent is extended or adjusted under 35 U.S.C. 154(b) by 0 days.

(21) Appl. No.: 09/359,891

(22) Filed: Jul. 26, 1999

(30) Foreign Application Priority Data

Jan. 28, 1997 (BE) ................................................ 9700078
Jan. 28, 1998 (WO) ................................ PCT/BE98/00014

(51) Int. Cl.[7] .................................................. G01N 21/89
(52) U.S. Cl. ....................................... 356/238.1; 356/430
(58) Field of Search ............................ 356/238.1, 238.3, 356/430, 238.2, 429; 250/559.4, 559.45

(56) References Cited

U.S. PATENT DOCUMENTS

| 3,841,761 | 10/1974 | Selgin . |
| 4,853,776 | 8/1989 | Itaya et al. . |
| 5,499,794 | * 3/1996 | Aeppli .............................. 250/559.45 |
| 5,768,938 | * 6/1998 | Schilling et al. ....................... 73/160 |

FOREIGN PATENT DOCUMENTS

| 1 938 083 | 2/1971 | (DE) . |
| 553 445 | 8/1993 | (EP) . |
| 553 446 | 8/1993 | (EP) . |
| 643 294 | 3/1995 | (EP) . |
| 652 432 | 5/1995 | (EP) . |
| 2 095 828 | 10/1982 | (GB) . |
| 93/19359 | 9/1993 | (WO) . |
| 95/29396 | 11/1995 | (WO) . |

* cited by examiner

Primary Examiner—Frank G. Font
Assistant Examiner—Layla Lauchman
(74) Attorney, Agent, or Firm—Pillsbury Madison & Sutro LLP

(57) ABSTRACT

The present invention relates to a detector (1) of foreign fibres and to a corresponding detection method, which can be used for detecting foreign fibres and foreign materials in a measurement object (5) in the textile industry, for example in yarns, slithers and unformed fiber bands on, for example, weaving machines, spinning machines, bobbin winding machines, doubling machines, cards, drawing benches and bobbin frames . . . . The principle of the detection is based on the fact that a measurement object (5) and foreign fibres or materials which are situated in the measurement object (5) absorb the light emitted into the measurement volume (4) by a light source (2) to different extents. All the light in the measurement volume (4), or a representative sample thereof, is measured by photodetectors (3) and converted into a photoelectric signal. Comparison of this signal with a signal measured when the measurement volume (4) was empty provides the absorption of the measurement object (5), from which the level of contamination of the measurement object (5) can be derived by interpretation.

31 Claims, 2 Drawing Sheets

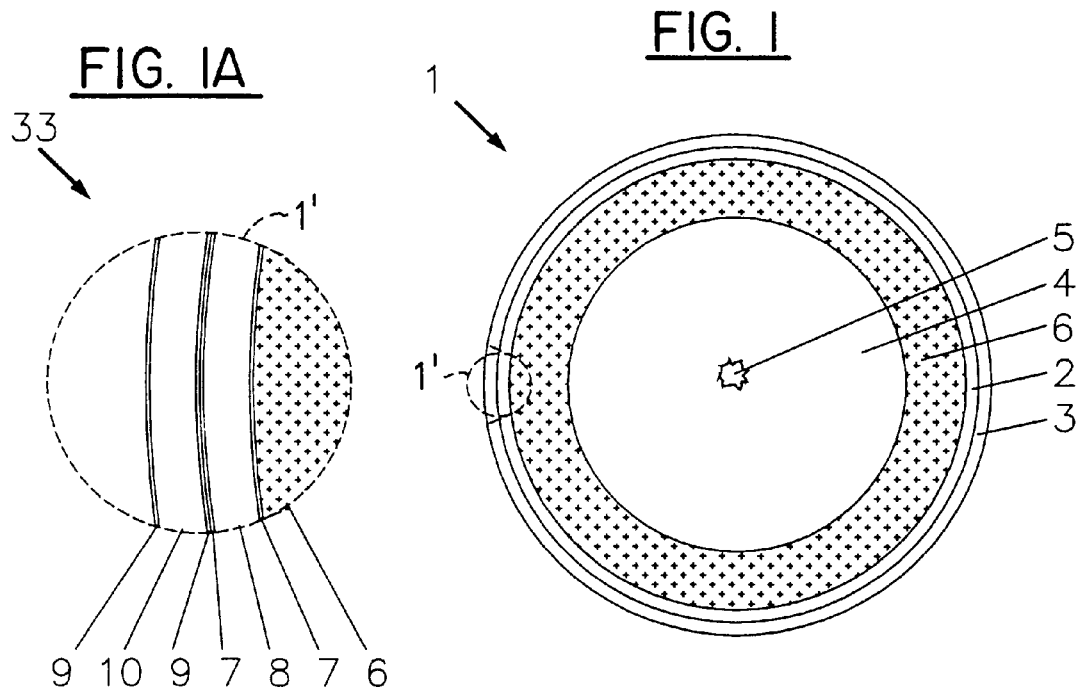
FIG. 1A
FIG. 1
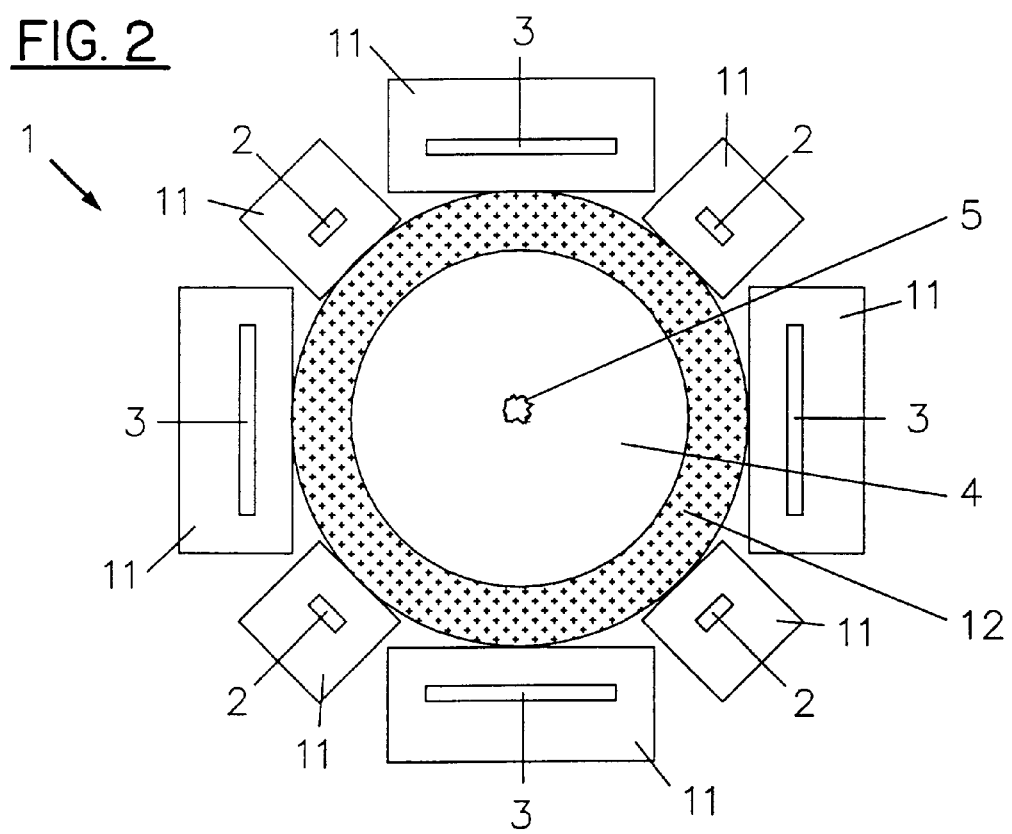
FIG. 2

DETECTION OF FOREIGN FIBRES AND FOREIGN MATERIALS BASED ON AN ABSORPTION MEASUREMENT OF LIGHT AND CORRESPONDING DETECTION METHOD

A detector of foreign fibres according to the present invention can be used for the detection of foreign fibres and foreign materials in the textile industry, for example in yarns, slivers and unformed fibre bands on, for example (though not exclusively), weaving machines, ring spinning machines, open-end spinning machines, air-jet spinning machines or chemical spinning machines, bobbin winding machines, doubling machines, cards, drawing benches, combing machines, bobbin frames, texturing machines, . . . .

In the rest of the description of the invention, yarns, slivers, unformed fibre bands and the like are referred to as the measurement object.

Existing detectors of foreign fibres are based on one of the following methods:

Detection of discoloration by detection in two or more spectral bands.

A method of this kind is described in WO 95/29396 (CSIRO). The measurement object is placed in front of a light-absorbing background, and at least one light source allows light with at least two different wavelengths to be incident on the measurement object, which reflects light. The light reflected by the measurement object contains at least two different wavelengths. The quantities of light of each wavelength are measured by one or more detectors, and these measured quantities of light are used to generate signals which are a function of the colour (or discoloration) of the measurement object. A similar approach is to be found in CH-A5-674379 (SCHEINHÜTTE), which document furthermore specifies that the influence of the diameter of the yarn on the reflected light is the same for both wavelengths and can in this way be eliminated.

Detection of contrast between the yarn and a matched background.

In EP-A-0 197 763 (CSIRO), the yarn to be examined is held in front of a background which is selected in such a way that it has a reflectivity which is approximately equal to that of the yarn itself. Diffused light illuminates the yarn and the background. The total quantity of light reflected by the yarn and by the background is measured at one location. If the background has been selected correctly, this quantity is virtually independent of the dimensions of the yarn to be examined. A change in the reflected light measured indicates the presence of contamination, and not a change in the dimensions of the yarn. As an alternative to a background of the same reflectivity as that of the yarn, the possibility is put forward of using a semi-transparent material as the background and illuminating through this material, so that the brightness detected by the receiver resulting from the background corresponds to the brightness resulting from the light reflected onto the yarn. This possibility is expanded on, inter alia, in EP-0,553,445 A2 (LOEPFE).

Detection of reflected light, normalized using diameter information.

A method of this kind is described, inter alia, in WO 93/13407 (SIEGFRIED PEYER AG). In this method, modulated light is directed from a light source onto the moving yarn. A first and a second sensor are provided, the first sensor receiving light which is reflected by the yarn, and the second sensor at the same time receiving light which is transmitted through the yarn. The transmitted light and the reflected light have opposite reactions to variations in the diameter of the yarn. The signals from the two sensors are combined with the aid of electronic means so that a signal is present at the output if there is a foreign fibre in the yarn and so that the effect of diameter variations is largely suppressed. Another embodiment of this method is described in WO 93/19359 (ZELLWEGER USTER AG).

EP-A-0,533,446 (GEBRÜDER LOEPFE AG) describes a method and an apparatus for the detection of contamination in yarns. In this method, a first sensor is used to measure light reflected by the yarn, resulting in a first measurement signal which is dependent on the magnitude of any contamination arising and on the diameter of the yarn. In order to eliminate the dependence on the diameter, a second measurement signal is recorded, which is dependent essentially only on the diameter of the yarn. A combination of the two measurement signals is used to compensate for the influence of the diameter of the yarn in the first measurement signal.

The principle of detecting foreign fibres and foreign materials on the basis of a colour measurement has the drawback that certain colours and discolorations with specific spectral reflection properties are not detected.

The principle based on contrast measurement against a background has the drawbacks that the background has to be matched to the yarn and also that this principle is unable to eliminate the influence of diameter variations of the measurement object itself to a sufficient extent. This drawback also applies to the principle according to which the reflection on the measurement object is normalized using diameter information. As a result, the sensitivity of these methods to foreign fibres and foreign materials is lower than desired.

The object of the detector according to the present invention is to provide a solution to the abovementioned drawbacks.

Principle

The detection method for detecting foreign fibres or foreign materials according to the invention is based on measuring the absorption of light which fills a measurement volume within which a measurement object is situated. Said absorption of light is measured without separately driving light sources for reflection and transmission, and without separately detecting signals representative for reflection and transmission. The spectrum of the light which is used for this purpose is selected in such a way that the measurement object does not absorb this light to a significant extent. Use is made of the fact that in that case foreign fibres and foreign materials will have a greater absorption coefficient for the spectrum of the light used than the measurement object itself.

The method is preferably carried out by introducing light into the measurement volume, in which the measurement object to be examined is situated, via at least one light source. Photodetection takes place in or around this measurement volume, with the result that all the light, or a representative sample of the light, inside the measurement volume is measured and converted into a proportional electrical signal. Comparison of this signal with a signal measured when the measurement volume was empty provides the absorption in the measurement volume, and interpretation of this provides the level of contamination of the measurement object.

The essential feature of the principle is the detection of all the light in the measurement volume, or of a representative sample thereof which is taken uniformly over the entire measurement volume. Furthermore, there are no specific conditions placed on the illumination, detection and measurement volume, in contrast to the principles currently used for the detection of foreign fibres and foreign materials, the correct functioning of which depends on the selection of the background, the setting of the background illumination or on an auxiliary signal for normalization.

In addition the present invention includes detection of foreign materials in a yarn on an open-end spinning machine, characterized in that the detection takes place at the level of the spinning tube. The detector used for the detection may be as described above. The elements of the detector may be arranged directly on the circumference of the spinning tube. The elements of the detector may also be arranged on a support which is attached to the outer wall of the spinning tube. The present invention also includes detection of foreign materials in a sliver at the level of the breaker or at the level of the rotor entry on an open-end spinning machine as well as detection of foreign materials in a sliver at the exit of a card or detection of foreign materials in a sliver at the entry to or exit from a drawing bench.

Operation

When the measurement volume is empty, there is no absorption of light in the measurement volume and all the light which is situated in the measurement volume, or a representative part thereof, is converted by photodetection into an electrical signal.

If a non-absorbing measurement object is situated in the measurement volume, again no light is absorbed; the light which is incident on the measurement object is, irrespective of the dimensions of the said measurement object, returned into the measurement volume until it is ultimately converted by photodetection into an electrical signal which is not different from the electrical signal with an empty measurement volume.

However, if the measurement volume contains a measurement object which is contaminated with a foreign fibre or foreign material, not all the light incident on the measurement object is then returned into the measurement volume. The light which is incident on the foreign fibre or the foreign material is partially absorbed thereby and the quantity of light detected is considerably less. The resulting electrical signal is significantly less than the electrical signal measured when the measurement volume was empty or with an uncontaminated measurement object.

If the measurement volume contains a measurement object whose absorption for the light used is non-negligible, the quantity of light in the measurement volume, and thus also the measurement signal, will be determined by the dimensions and absorption of the measurement object. If the dimensions do not change, the measurement signal can still always be used as a measure of the contamination.

Processing of the signal

In contrast to conventional detectors of foreign fibres and foreign materials, only a very simple circuit (signal-processing unit) is needed in order to allow the detector according to the invention to operate: it is sufficient to activate the light source using the correct electric current (for example using a direct current for an LED), and to amplify the photoelectric signal to a usable level using a suitable amplifier.

The absolute value of the light detected can be used to derive an absolute measure of the absorption of the light employed by the measurement object. In another approach, which takes account only of the variation of the light detected, the relative absorption can be derived by comparison with an uncontaminated measurement object.

By evaluating the level of the electrical signal, it is possible to establish whether a foreign fibre or foreign material is present in the measurement volume and hence in the measurement object.

This evaluation can lead to assigning a contamination index in an automated manner to the measurement object, by associating a contamination index with each absorption.

The electrical signal can be processed further in a conventional manner by means of analog or digital circuits or using programmable digital signal processing or microprocessor circuits. It is thus possible to take into account the amplitude and the length of the deviation, for example in order to decide whether it is necessary to interrupt the movement of the measurement object or the processing which the measurement object is undergoing, in order to remove the deviating parts from the measurement object, or for statistical characterization of the measurement object. Processing and using the signals in this way is usual both for detectors of foreign fibres which are based on other principles and for measurement equipment based on diameter or mass measurements which is known from the prior art.

Light source

The spectrum of the measurement light has a considerable influence on the types of foreign fibres and foreign materials which can be detected using the detector according to the invention. This is linked to the spectral absorption properties of these contaminating materials.

Some foreign fibres and foreign materials in the measurement object can be perceived visually as a change in intensity or a discoloration. Extensive tests have demonstrated that this visible contamination can best be detected using yellow or green measurement light.

Other foreign fibres and foreign materials cannot be distinguished visually from the measurement object, but are of a different type of material. A frequently occurring contamination of cotton is, for example, polypropylene. Both look virtually white in their natural form. However, it is possible to distinguish the two materials from one another both in ultraviolet and in near infrared by their different specific absorption of this light. By selecting the appropriate wavelength or band of wavelengths of the measurement light, it is possible to detect foreign fibres and foreign materials on the basis of the type of material instead of on the basis of their colour. The wavelengths at which the types of material differ in absorption are typically situated in the near infrared between 1000 nm and 5000 nm.

The light source used in the present invention does not necessarily have to be a light-emitting diode, also known as LED, but may also be an incandescent lamp or an arc lamp which fills the measurement volume with light, either directly or indirectly, via one or more optical conductors.

As an alternative light source, it is possible to use, for example, electroluminescent materials. A layer of a material of this kind is applied to a substrate. This substrate may take the form of a cylinder. In order to make the sensitivity uniform over the measurement volume, the light source is preferably disposed in such a way that the space inside the measurement volume is illuminated uniformly.

The measurement light emanating from the light source may optionally be intensity-modulated. By intensity modulation of the measurement light at a specific frequency, it is possible to distinguish it from ambient light and thus to suppress the latter effectively.

Photodetection

One or more photosensitive elements can be used for the photodetection. Their number is not essential, but it is necessary that there is an arrangement which allows all the light in the measurement volume, or a representative sample thereof, to be measured. The photosensitive elements used must be sufficiently sensitive to the spectrum of the measurement light emitted by the light source.

The photodetectors may, for example, be silicon photodiodes, but the invention is not limited to such detectors. These photodiodes are suitable for the detection of light in the visible spectrum and the near infrared (typically 400 to 1100 nm). Other photodetectors are known to the person skilled in the art for both shorter wavelengths (UV) and for longer wavelengths (IR), such as for example germanium or InGaAs photodiodes.

Photodiodes are mostly constructed as discrete components. The current state of technology also allows photodetectors to be applied to a substrate in the form of an active layer. It is conceivable that this substrate may adopt a form which adjoins the measurement volume or forms the measurement volume, such as for example, although not exclusively, the form of a cylinder. This method is a perfect addition to the approach using an electroluminescent light source, which as stated above is also applied to a substrate in the form of an active layer.

Measurement volume

The shape of the measurement volume should allow all the light present, or a representative sample thereof to be measured by photodetection. This shape may, for example, be a sphere or a cylinder. One or more openings are provided in the measurement volume in order to allow the measurement object to enter and leave the measurement volume. According to a possible embodiment, this opening takes the form of a slot. On the other hand, it is possible to provide two openings in a sphere or cylinder, respectively for the entry and exit of the measurement object.

The boundary of the measurement volume is resistant to the friction caused by the measurement object. It is preferably dirt-repellent and easy to clean. It is made from a material which is transparent to the measurement light or transmits the latter if the light source(s) and/or detector(s) are placed outside the measurement volume. It is however fully reflecting keeping the light inside the measurement volume if light source(s) and detector(s) are placed inside the measurement volume.

The measurement volume may be positioned anywhere in the normal path of the measurement object, either as an extra component or to replace or supplement components which are already present in the path.

Use of a plurality of colours or wavelengths or bands of wavelengths

If one colour or wavelength or band of wavelengths is used, it may be that a number of different contaminating materials of the measurement object will be difficult or impossible to detect. For this reason, as an extension to the present invention it is possible to use illumination which comprises a plurality of colours or wavelengths or bands of wavelengths. The combination can be optimized for the detection of specific contaminants.

To this end, it is possible to use the light from one or more broad-band light sources, such as for example an arc lamp or incandescent lamp, the spectral distribution of which is optionally adapted to the requirements by active or passive optical filtering.

As an alternative, it is possible to use a combination of light sources, different light sources or groups of light sources each emitting light of a different colour or wavelength or band of wavelengths.

With illumination of this kind, the detection can be carried out by measuring the total resulting quantity of light in the measurement volume, or a representative, uniform sample thereof. This is used to obtain a total weighted absorption for the colours or wavelengths or bands of wavelengths used.

As an alternative, the absorption can be measured separately for the various colours or wavelengths or bands of wavelengths. In order to separate the signals detected for these various colours or wavelengths or bands of wavelengths from one another, the light sources or groups of light sources which emit a different colour or wavelength or band of wavelengths can be switched on and off sequentially or can be intensity-modulated at a different frequency. The signals can be separated from one another using synchronous detection or electronic filtering.

Separation into different colours or wavelengths or bands of wavelengths is also possible by means of active or passive optical filters which are placed in front of one or more photosensitive elements.

The only essential factor is that all the light present in the measurement volume, or at least a representative sample thereof, is detected for each colour or wavelength or band of wavelengths.

The invention will be described in more detail with reference to the figures, in which:

FIGS. 1 and 1A show a first detector according to the invention,

FIG. 2 shows a second detector according to the invention,

Figure 3:
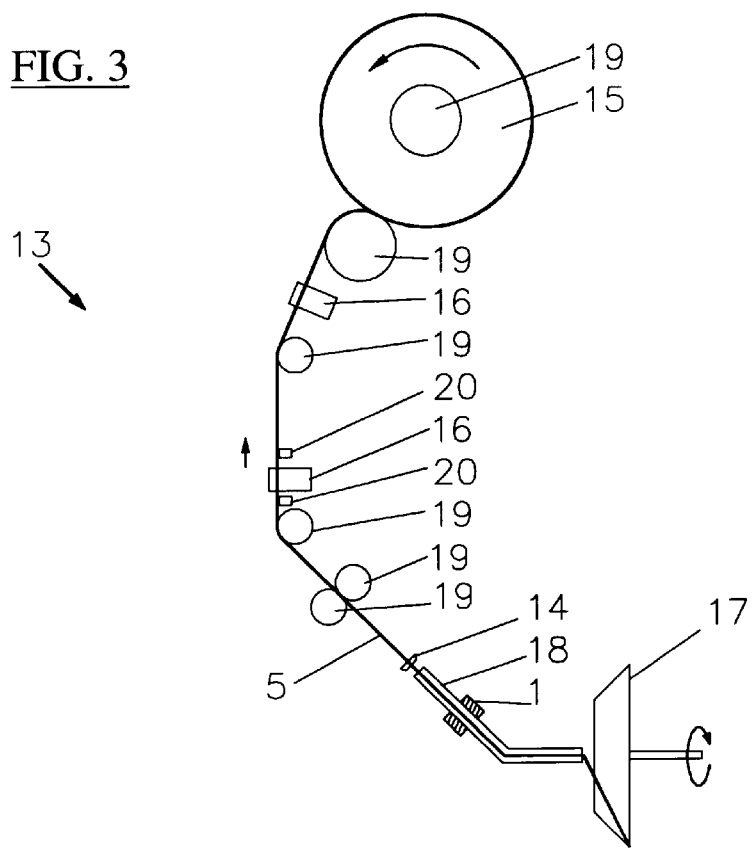
FIG. 3 shows a diagrammatic illustration of the path of the yarn in an open-end spinning machine.

FIG. 1 and FIG. 2 each show a detector 1 according to the invention. They each comprise at least one light source 2 and one or more photodetectors 3 which enclose a measurement volume 4. Both the light source 2 and the photodetectors 3 are situated around the measurement volume 4, through which a measurement object 5 to be examined is passing.

Application

FIG. 3 shows a diagrammatic illustration of the path 13 of the yarn in an open-end spinning machine. In the following text, a discussion is given, as a typical application of the invention, of a detector 1 for detecting foreign fibres and foreign materials in a measurement object 5, which is a yarn spun on an open-end spinning machine. A person skilled in the art is able to modify this embodiment for other applications, such as other types of spinning machines, bobbin winding machines, doubling machines, cards, combing machines, texturing machines, weaving machines, . . . .

Known detectors 16 are usually placed on an open-end spinning machine in the path of the yarn between the navel 14 and the bobbin 15. The yarn 5 is wound onto the bobbin 15 from the navel 14 via drive and guide rolls 19. Owing to their position, known detectors 16 in the path of the yarn are always provided with some form of slot, along which the yarn 5 is introduced into the measurement slot of the detector 16. Supports 20 ensure that the position of the yarn 5 in a detector 16 is stable. In the current embodiment, detectors of foreign fibres are integrated with the equipment for measuring diameter or mass. The detection method described here can likewise be carried out in this way. However, a significant problem is that there is not sufficient space available for this on every type or model of open-end spinning machine.

In addition to being placed in the path of the yarn, a detector 1 based on absorption measurement can also be placed on open-end spinning machines between the navel 14 and the rotor 17 itself, where the so-called "spinning tube" 18, a tubular element which is essential to the open-end spinning process, forms a channel which guides the yarn outwards from the rotor 17.

The tubular shape of the spinning tube 18 corresponds extremely well to the requirements of an ideal measurement volume. The detector 1 is placed on the spinning tube 18 or integrated therewith. This has a number of advantages:

- it can be used on open-end spinning machines of any design
- self-cleaning properties, owing to the subatmospheric pressure from the rotor 17 and owing to the friction of the yarn 5
- material of the spinning tube 18 can be selected as a function of the requirements of the detector 1
- abundance of space
- inherent protection from ambient influences.

Selecting the spinning tube 18 as the measuring position implies a cylindrical measurement volume 4.

Spinning process demands, such as a specific finish, are placed on the inner wall of the spinning tube 18. The only demands which the spinning machine places on the outer circumference of the spinning tube 18 are technical assembly demands. For this reason, the components of the detector 1 are arranged on the outer circumference of the spinning tube 18. This means that the material forming the spinning tube 18 must be transparent or light-transmitting for the measurement light emanating from the light source 2. There is sufficient space and capacity to supplement and adapt the spinning tube 18 for the mounting of a detector 1.

First preferred embodiment

In a first preferred embodiment in accordance with FIG. 1, the spinning tube 18 is designed with a transparent wall 6.

On the outer circumference of this wall 6, there is first arranged a light source 2, which comprises two light-transmitting electrodes 7 and an active layer 8. The active layer 8 consists, for example, of an electroluminescent material. This material is transparent or light-transmitting to the light emitted.

Above these layers is a light-sensitive layer 3, which comprises two transparent electrodes 9, between which is situated a photodetection layer 10. The photodetection layer 10 preferably comprises a photodiode produced from amorphous silicon. The structure of the layers is made clearer by an enlarged detail 33 from detector 1 in FIG. 1.

By completely surrounding the measurement volume 4 with a photodetector 3, this arrangement fulfils the requirement of detecting all the light in the measurement volume 4.

Second preferred embodiment

In a second preferred embodiment in accordance with FIG. 2, silicon photodiodes which are produced from monocrystalline silicon are used as photodetectors 3. It is ensured that the circumference of the measurement volume 4 is surrounded as completely as possible by the various silicon photodiodes.

These photodiodes are selected in such a way that they are sensitive to the light which is emitted by the light source 2 used in the detector 1.

A non-absorbing optical diffuser 12 is placed between the measurement volume 4 and the photodetectors 3. To this end, a non-absorbing, optically diffusing material is used for the wall of the spinning tube 18. All the light in the measurement volume 4 is ultimately incident on the diffuser 12. The spatial properties of that light are averaged out statistically in the diffuser 12. Some of this light is incident on the photodetectors 3, via the diffuser 12. In this way, a sample of all the light in the measurement volume 4 is measured, and the sample is taken uniformly over the entire measurement volume 4, with the result that this second preferred embodiment satisfies the requirements. In this way, the effect of the non-sensitive locations between the photodetectors 3, caused by the planar design of these photodetectors 3 and of the light sources 2, is eliminated.

Light-emitting diodes (LEDs) are used as the light source 2. In principle, one LED is sufficient for the detector 1 to function, but the greater quantity of light introduced into the measurement volume 4 by a plurality of LEDs provides a greater electro-optical signal-noise ratio.

The light sources 2 are placed between the photodetectors 3 and illuminate the measurement volume 4 through the diffuser 12.

Yellow LEDs are preferably used, owing to their high efficiency together with their absorption by most coloured foreign fibres and foreign materials.

The electro-optical components of the detector 1 can be arranged on the spinning tube 18 in various ways. A first possibility is to attach the light sources 2 and the photodetectors 3 directly on the circumference. Another possibility is first to apply the components to a support, which is in turn attached to the outer wall of the spinning tube 18.

Signal processing

Figure 4:
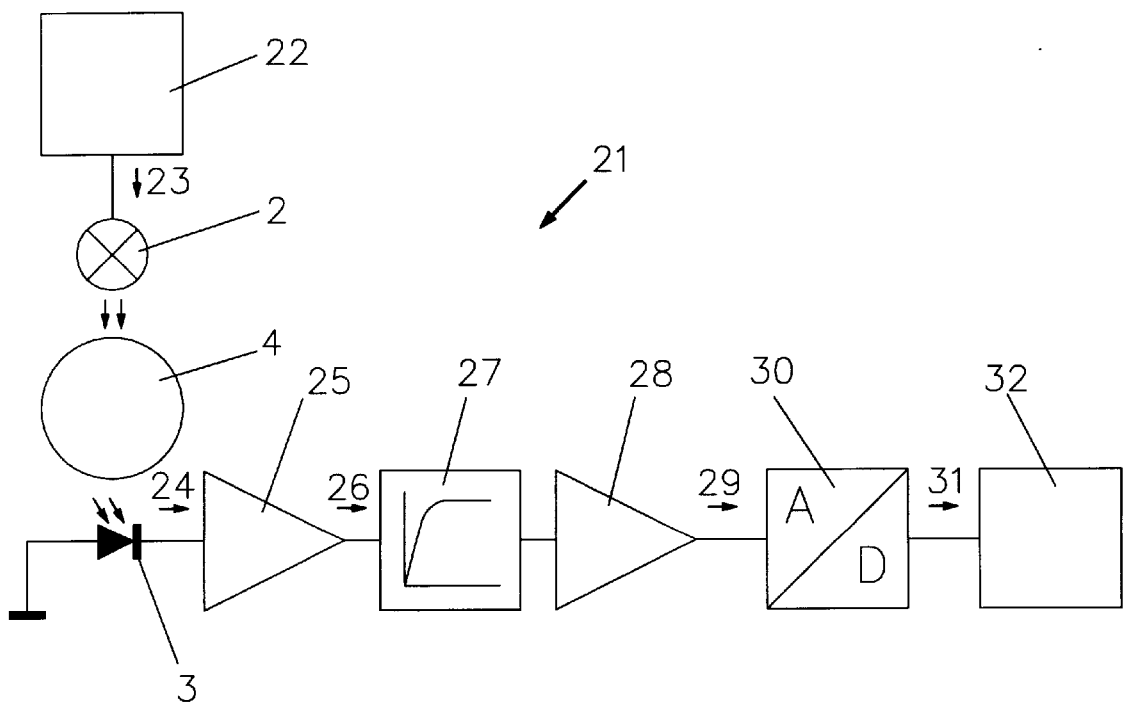
FIG. 4 shows a diagrammatic illustration of the control system of a detector according to the invention.

Both preferred embodiments of this invention are controlled in the same way. By way of example, although not by way of limitation, the signal processing can be carried out in accordance with FIG. 4.

Control circuit 22 is used to send a current 23 through the light source 2. As a result, the light source 2 emits light into the measurement volume 4.

The components indicated by reference numerals 24 to 32 together form the signal-processing unit 21.

The signal current 24 from the photodetectors 3 is amplified with the aid of an amplifier 25. The amplified signal 26 is proportional to the absorption measured.

The variations in the amplified signal 26 are amplified, via a high-pass filter 27, in an AC voltage amplifier 28. The output signal 29 from the AC voltage amplifier 28 is proportional to the variation in the absorption.

This output signal 29 from the AC voltage amplifier 28 is fed to an analog-to-digital converter 30. The data 31 from the analog-to-digital converter 30 are processed further by a programmable digital computer 32.

What is claimed is:

1. Method for the detection of foreign materials in a measurement object, comprising:

- illuminating the measurement object in a measurement chamber, the measurement chamber surrounding the measurement object, or surrounding the measurement object except for one or more slots, there being at least one light source for illuminating the measurement object;
- detecting at least a representative sample of the light having one or more wavelengths inside the measurement chamber which is taken uniformly over the entire measurement chamber;
- generating an electrical signal in accordance with the light having one or more wavelengths detected in the detecting step;
- deriving from the electrical signal an absorption value of absorption by the measurement object of the light having one or more wavelengths in the measurement chamber by determining the amount of light having one or more wavelengths lost from the measurement chamber; and
- determining from said absorption value whether foreign material is present in the measurement object.

2. Method according to claim 1, wherein the at least one light source comprises light sources for reflection and transmission, the light sources for reflection and transmission are not driven separately, reflected light and transmitted light are not detected separately, and reflections of background and measurement object are not necessarily matched.

3. Method according to claim 1, including selecting a wavelength or a band of wavelengths of the light emitted by the at least one light source in such a way that types of material in the measurement object are distinguishable.

4. Method according to claim 1, including choosing the spectrum of the light having one or more wavelengths so that the absorption by the measurement object of this light is less than the absorption by a foreign material.

5. Method according to claim 1, including choosing the spectrum of the light having one or more wavelengths so that the measurement object does not absorb this light to a significant extent.

6. Method according to claim 1, further including:
generating the electrical signal by conversion of the detected light, the electrical signal being proportional to the detected light;
comparing this signal with a signal measured when the measurement chamber is empty and generating a value for the absorption of the light by the measurement object from the comparison, and
determining the level of contamination by foreign materials in accordance with the absorption value.

7. Method according to claim 1, wherein the light introduced into the measurement chamber has a plurality of wavelengths or several bandwidths and said deriving comprises deriving a value for a weighted absorption of the plurality of wavelengths or several bandwidths of light by the measurement object.

8. Method according to claim 1, wherein the light which is introduced into the measurement chamber is light of more than one color or wavelength or band of wavelengths, and said method includes deriving the absorption value separately for each color or wavelength or band of wavelengths.

9. Method according to claim 6, including assigning a contamination index to the measurement object in accordance with the level of contamination.

10. Method according to claim 1, wherein when the measurement object is in motion or is being processed, the method further comprising stopping the movement or processing when a foreign material is detected in the measurement object.

11. Detector for detecting foreign materials in a measurement object which is situated in a measurement chamber, the measurement chamber surrounding the measurement object or surrounding the measurement object except for one or more slots, comprising:
at least one light source which emits light into the measurement chamber,
one or more photodetectors which convert light having one or more wavelengths in the measurement chamber into an electrical signal, and
a signal processing unit,
the one or more photodetectors being disposed in such a manner that they intercept at least a representative sample of the light having one or more wavelengths present in the measurement chamber taken uniformly over the entire measurement chamber;
said signal processing unit comprising means for deriving from the electrical signal obtained by photodetection a value for the absorption of the light having one or more wavelengths in the measurement chamber by the measurement object and for determining whether there are foreign materials present in the measurement object based on the absorption value.

12. Detector according to claim 11, wherein the wavelength or band of wavelengths of the light emitted by the light source is selected such that different types of material have different absorbencies of the light.

13. Detector according to claim 11, wherein the spectrum of the light having one or more wavelengths is absorbed less by the measurement object than by a foreign material.

14. Detector according to claim 11, wherein the spectrum of the light having one or more wavelengths is not absorbed by the measurement object to a significant extent.

15. Detector according to claim 11, wherein the light source is selected from an LED, an incandescent lamp and an arc lamp.

16. Detector according to claim 11, wherein the light source is an electroluminescent layer.

17. Detector according to claim 11, wherein the light source emits yellow or green light.

18. Detector according to claim 11, wherein the one or more photodetectors are silicon photodetectors.

19. Detector according to claim 11, wherein the one or more photodetectors are vacuum-deposited on a substrate.

20. Detector according to claim 11, wherein the light emitted by the light source is intensity-modulated.

21. Detector according to claim 11, wherein the measurement chamber is a slot.

22. Detector according to claim 11, wherein the measurement chamber is a sphere or a cylinder provided with at least one opening in order to allow the measurement object to enter the measurement chamber.

23. Detector according to claim 11, wherein the boundary of the measurement chamber is a light-transmitting wall.

24. Detector according to claim 11, wherein a diffuser is situated between the measurement chamber and the one or more photodetectors.

25. Use of a detector as described in claim 11 for detection of foreign fibers or foreign materials on one of the machines selected from a card, a drawing bench, a ring spinning machine, an air-jet spinning machine, an open-end spinning machine, a chemical spinning machine, a bobbin winding machine, a doubling machine, a combing machine, a bobbin frame, a texturing machine, a loom.

26. Apparatus for detecting foreign materials in a yarn on an open-end spinning machine comprising a detector as in claim 11, dispersed to effect detection at a spinning tube.

27. Apparatus according to claim 26, wherein elements of the detector are arranged directly on a circumference of the spinning tube.

28. Apparatus according to claim 26, wherein the elements of the detector are arranged on a support which is attached to an outer wall of the spinning tube.

29. Apparatus for detecting foreign materials in a sliver comprising a detector as in claim 11 wherein the detection is carried out at the level of one of a breaker and a rotor entry on an open-end spinning machine.

30. Apparatus for detecting foreign materials in a sliver comprising a detector as in claim 11, wherein the detection is carried out at an exit of a card.

31. Apparatus for detecting foreign materials in a sliver comprising a detector as in claim 11, wherein the detection is carried out at an entry to or an exit from a drawing bench.

* * * * *

UNITED STATES PATENT AND TRADEMARK OFFICE
CERTIFICATE OF CORRECTION

PATENT NO. : 6,201,602 B1
DATED : March 13, 2001
INVENTOR(S) : Bouvyn

Page 1 of 1

It is certified that error appears in the above-identified patent and that said Letters Patent is hereby corrected as shown below:

Title page,
Under "Item [30] FOREIGN APPLICATION PRIORITY DATA" please delete
-- Jan. 28, 1998 (WO)...........PCT/BE98/00014 --
Please insert -- Related U.S. Application Data [63] Continuation of international application No. PCT/BE98/00014, Jan. 28, 1998 --

Signed and Sealed this

Twenty-ninth Day of January, 2002

Attest:

Attesting Officer

JAMES E. ROGAN
*Director of the United States Patent and Trademark Office*